US006295657B1

(12) United States Patent
Prue

(10) Patent No.: US 6,295,657 B1
(45) Date of Patent: Oct. 2, 2001

(54) ADJUSTABLE ADDITIVE INJECTION UNIT FOR A MARINE TOILET SYSTEM

(76) Inventor: Frederick C. Prue, 173 Berkeley St., North Andover, MA (US) 01843

(*) Notice: Subject to any disclaimer, the term of this patent is extended or adjusted under 35 U.S.C. 154(b) by 0 days.

(21) Appl. No.: 09/450,353

(22) Filed: Nov. 29, 1999

Related U.S. Application Data

(60) Provisional application No. 60/119,182, filed on Nov. 30, 1998.

(51) Int. Cl.[7] .................... E03D 9/02; A61L 2/16
(52) U.S. Cl. .................... 4/222; 222/522; 285/61
(58) Field of Search .................... 4/222, 222.1, 223, 4/224, 225.1, 226.1, 227.1, DIG. 7; 285/11, 121.3, 127.1, 133.3, 274, 61–64; 137/205.5, 268; 222/522

(56) References Cited

U.S. PATENT DOCUMENTS

| 215,987 | * | 5/1879 | Spofford | 285/64 |
|---|---|---|---|---|
| 685,694 | * | 10/1901 | Schamp | 285/64 |
| 1,593,268 | * | 7/1926 | Roberts | 285/63 |
| 1,910,765 | * | 5/1933 | Hanlan | 285/61 |
| 2,303,913 | * | 12/1942 | Collinge et al. | 4/224 |
| 4,873,727 | * | 10/1989 | Homan | 4/226.1 |
| 4,920,582 | * | 5/1990 | Alker | 4/DIG. 7 |
| 5,142,707 | * | 9/1992 | Prue | 4/222 |
| 5,240,292 | * | 8/1993 | Roszin | 285/64 |
| 5,404,594 | * | 4/1995 | Ring et al. | 4/226.1 |

FOREIGN PATENT DOCUMENTS

| 468282 | * | 6/1937 | (GB) | 4/226.1 |
|---|---|---|---|---|

* cited by examiner

*Primary Examiner*—Charles R. Eloshway
(74) *Attorney, Agent, or Firm*—Charles G. Call

(57) ABSTRACT

A unit for injecting a disinfectant, deodorant or the like into the inlet stream of flushing water as it is pumped into the bowl of a tankless marine toilet. The injection unit is preferably constructed of commercially-available plastic plumbing components. The main body of the unit provides an additive reservoir which surrounds the flush water inlet pipe and is formed from a conventional plastic sanitary tee jointed fitted at each end with plastic size-reduction bushings. The two bushings connect the injection unit to the flush water inlet tubing and also support an interior flow pipe. Holes drilled at angles in the flow pipe divert a portion of the flush water through the additive reservoir where it mixes with and dissolves the additive (normally a water soluble disk of the type typically placed in the tank of a household toilet). Slidable plastic bushings surrounding the interior flow pipe may be axially moved to adjust the size of fluid passageways to vary the amount of diverted fluid and hence the amount of additive injected into the flush water stream. A pair of cup-shaped mounting yokes are mounted for independent rotational movement at each end of the main body of the unit, permitting the unit to be oriented as desired and attached to a variety of available wall and bulkhead surfaces.

5 Claims, 4 Drawing Sheets

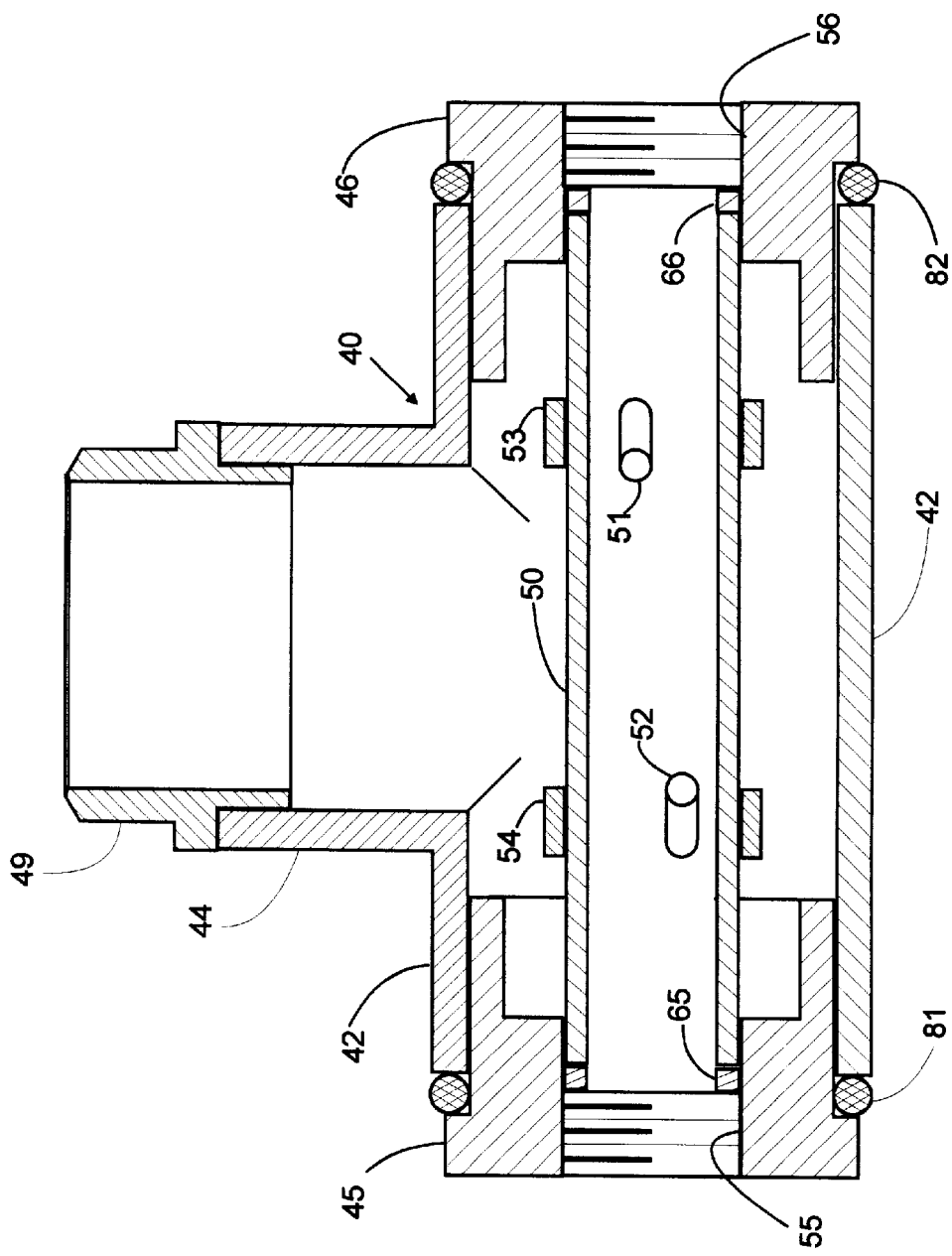
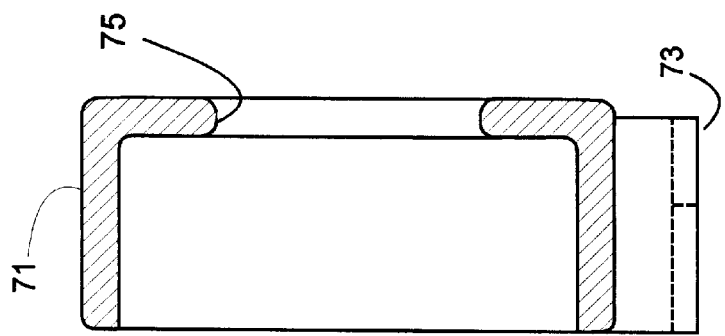

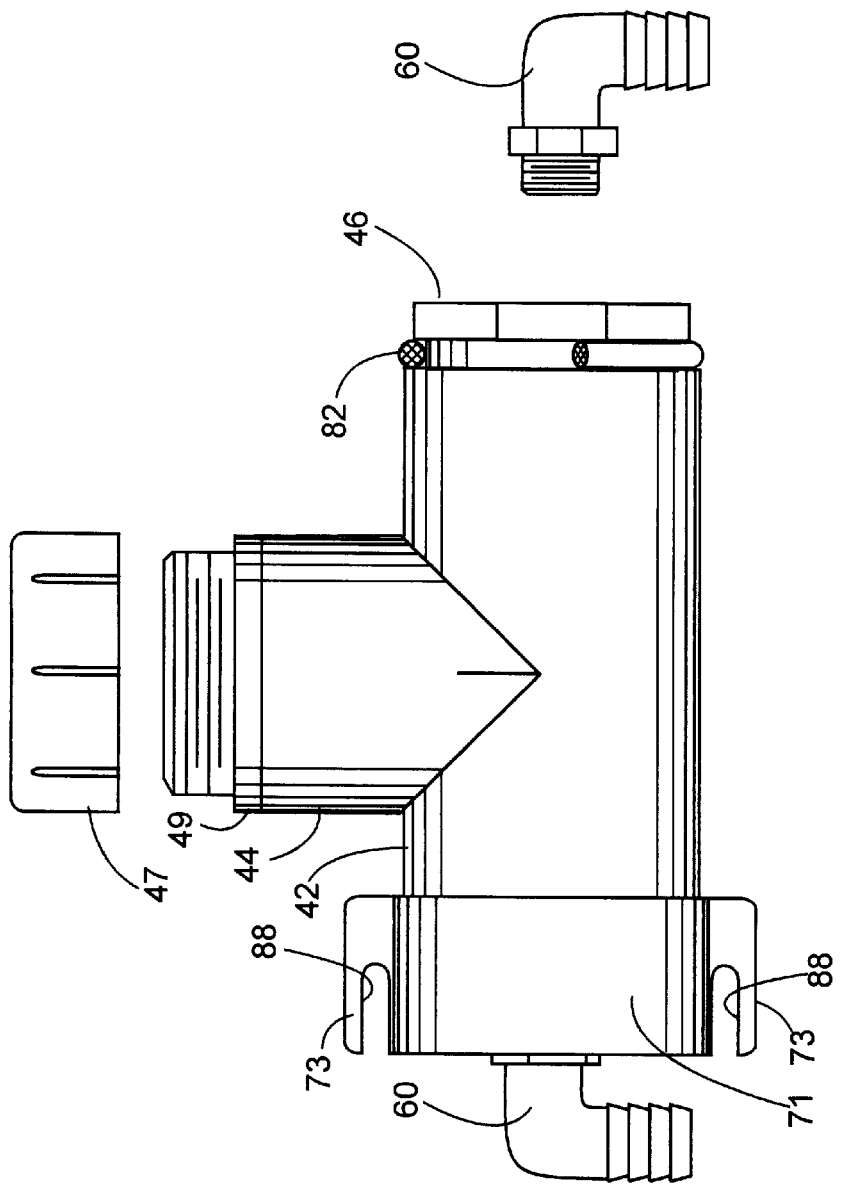
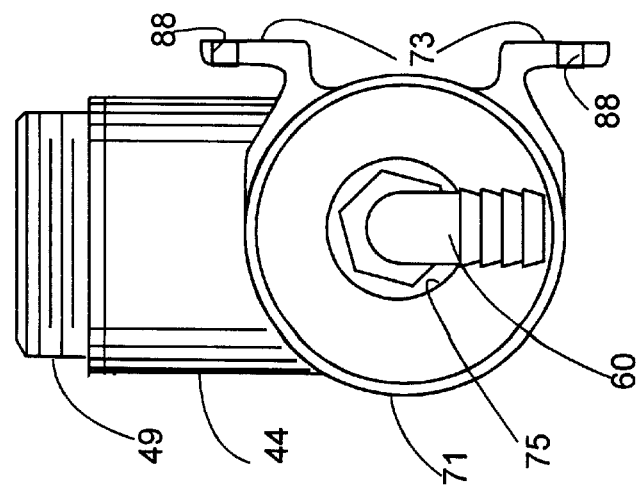
Fig. 4    Fig. 5    Fig. 6

ADJUSTABLE ADDITIVE INJECTION UNIT FOR A MARINE TOILET SYSTEM

CROSS-REFERENCE TO RELATED APPLICATION

This application claims the benefit of the prior filed U.S. Provisional Application Ser. No. 60/119,182 filed on Nov. 30, 1998.

FIELD OF THE INVENTION

This invention relates to a device for introducing additives into a fluid flow and, more specifically, to an adjustable mounting arrangement for installing an additive injector which combines sanitizing, deodorizing, lubricating or winterizing additives with the flush-water flow into a tankless toilet of the type used in pleasure boats and travel trailers.

BACKGROUND OF INVENTION

Conventional household toilets have a flush-water holding tank typically mounted above the toilet bowl. The holding tank is filled to a preset level with water so that, when the toilet is flushed, a substantial quantity of water is available to provide a thorough flushing action. Marine toilets typically installed in pleasure craft have no tank. Instead, a flushing pump is used to propel flushing water though a water supply conduit which extends from an intake opening in the boat's hull. In this way, seawater rather than fresh water can be used to flush the toilet, reducing the size and weight of the toilet and avoiding unnecessary consumption of the on-board supply of fresh water.

Although the conventional "tankless" marine toilet performs its basic functions satisfactorily, it has significant shortcomings. Standing water in the toilet system often creates odors which are particularly unpleasant in the small and poorly ventilated confines of the craft's cabin space. The use of seawater for flushing, rather than fresh water, aggravates the problem because seawater typically contains salt, microorganisms, plant life, and other contaminants which often intensify the odors.

U.S. Pat. No. 5,142,707 issued to Frederick C. Prue on Sep. 2, 1992, the disclosure of which is incorporated herein by reference, describes an highly effective additive injector that can be used to deodorize, lubricate and clean a tankless marine toilet system. That arrangement as described in the Prue patent is typically connected in the flush water intake as indicated generally at 11 in FIG. 1 of the drawings. The injection unit 11 is serially connected with a flush water conduit 13 which carries flushing water from a through-the-hull intake port 15 to a toilet bowl 19. A gate valve 20 connects the conduit 13 to the intake port 15. When closed, the valve 20 prevents sea water from entering the toilet system via the intake port 15.

Waste from the toilet bowl 19 flows through a drain conduit 21 and then passes either through a gate valve 23 to a through-the-hull outlet port 25, or alternatively through a gate valve 27 to a collection tank 31. When the waste is to be expelled through the outlet port 25, the gate valve 23 is open and the valve 27 is closed. When the waste is to be placed in the collection tank 31, valve 23 is closed and valve 27 is opened. Collection tank 31 is provided with a vent 33 and a waste removal conduit 35 which extends to a deck plate 37 which provides access to the collection tank for waste removal. In order to provide an adequate flow of flushing water, a hand-operated flushing pump of the type illustrated at 35 in FIG. 1 may be serially connected with the flush water conduit 13 adjacent the toilet bowl 19. Other pumping mechanisms may be employed, both in the flush water intake and in the outlet drainage conduits, to provide the desired flows.

While the additive injection unit as described in U.S. Pat. No. 5,142,707 and shown in FIG. 1 has proven to be highly effective, it is often difficult to securely install. The marine toilet and the input water line into which the additive injector must be installed are typically placed in a cramped environment, and adjoining bulkhead or cabin walls can be oriented in many different ways, making it difficult to properly secure the injector while positioning it in an orientation which best promotes proper functioning and access.

It is accordingly a general object of the present invention to provide an improved additive injection unit which is easy to install and use for sanitizing, deodorizing, lubricating and/or winterizing a marine toilet system.

It is a further object of the present invention to provide an additive injection unit which may be readily mounted in the a desired position by securing it to an existing structure which may have any one of a wide variety of orientations.

It is a further object to provide an improved marine toilet additive injection unit including integral adjustable mounting means for securing the unit in the proper position within an existing marine toilet system.

SUMMARY OF THE INVENTION

The present invention takes the form of an improved additive injection unit for a toilet system which includes an elongated housing defining a passageway for carrying a water stream directed to a toilet and for injecting an additive into said water stream, the unit being mountable in a variety of toilet system environments by the provision of first and second mounting members attached to each end of said housing, each of the mounting members being rotatable with respect to the housing and defining a mounting surface adapted to bear against and be supported by a base structure.

In accordance with the invention, the housing advantageously takes the form of a substantially T-shaped hollow chamber and defines a transverse cylindrical passageway and a perpendicular cylindrical branch passageway, with the mouth of the branch passageway forming the access opening through which an additive may be introduced. Each of the mounting brackets includes a hollow cylindrical section shaped to fit over and conform to one end of the transverse passageway. A resilient O-ring positioned between each of mounting brackets and the housing for providing a friction fit between the mounting brackets and the housing which permits the mounting brackets to both rotate and move axially with respect to the housing.

The additive injection unit preferably includes a cap for covering the access passageway to retain fluids within the housing while permitting access to the interior of the housing when removed. The rotatable mounting brackets permit the housing to be rotated with respect to the base structure to position the access opening above the transverse passageway to reduce spillage when the cap is removed. These and other features and advantages of the present invention may be better understood by considering the following detailed description. In the course of this description, frequent reference will be made to the attached drawings.

BRIEF DESCRIPTION OF THE DRAWINGS

FIG. 2 is a side cross-sectional view showing the interior details of the body of the improved additive injection unit embodying the present invention;

FIG. 3 is an side cross-sectional view of one of the two rotatable mounting yokes which are fitted to each end of the additive injector to secure it to a bulkhead or the like;

FIG. 4 is an end elevational view of the injector unit;

FIG. 5 is a side elevational view of the injector unit;

FIG. 6 is a side elevational view of a angled hose connector shown separately from the injector unit.

DESCRIPTION OF THE PREFERRED EMBODIMENT

Figure 1:
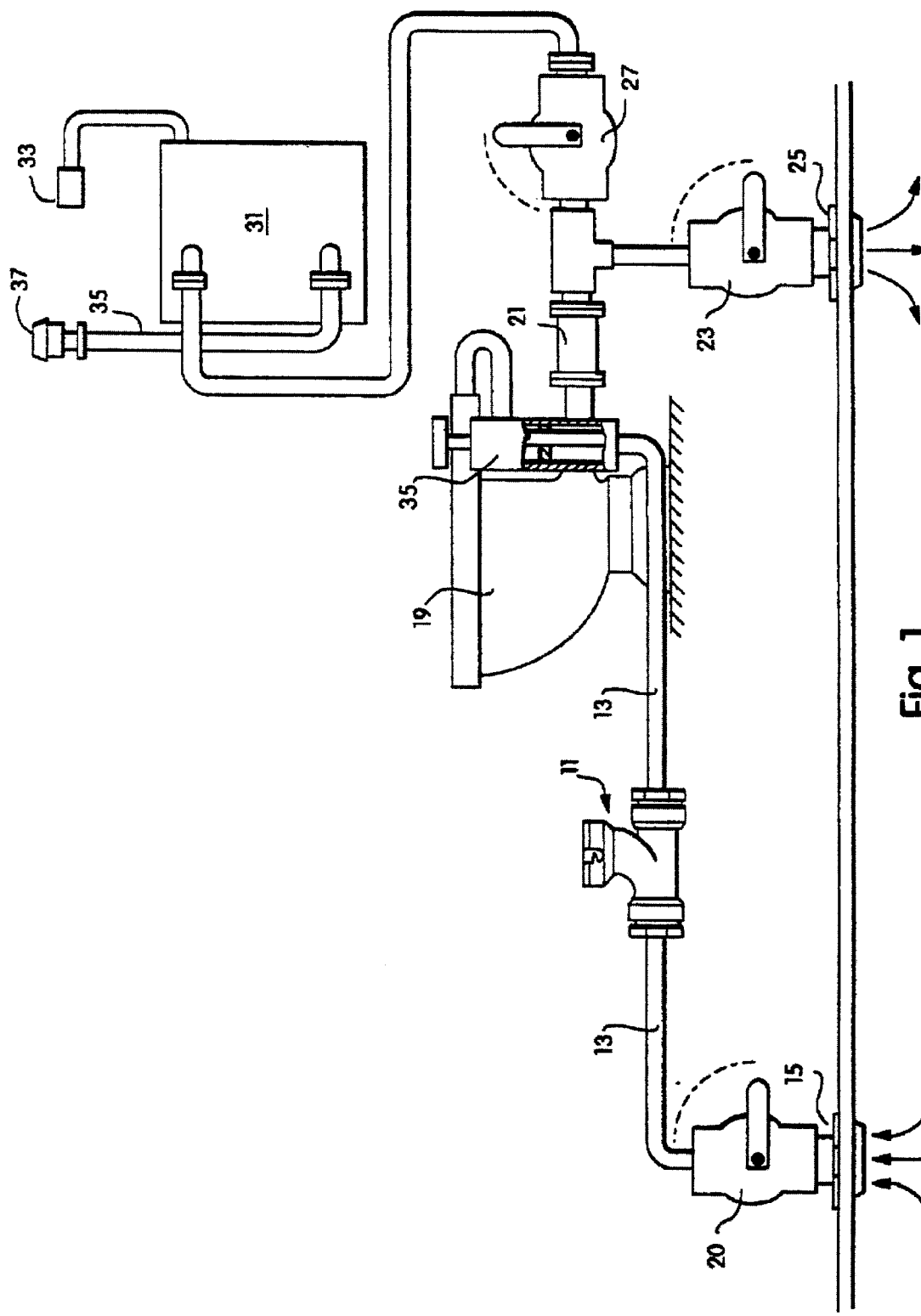
FIG. 1 depicts a prior art additive injection unit installed in a marine toilet system.

FIG. 2 of the drawings provides an enlarged view of the exterior of the body an additive injection unit which embodies the present invention. The main body of the unit is formed by a conventional sanitary pipe tee joint 40 having a transverse pipe section 42 and an outwardly extending branch section 44. The opposing ends of the transverse section 42 terminate at mouth openings into which standard size-reduction bushings 45 and 46 are fitted. The mouth opening at the end of the branch section 44 is sealed with a twist-on sealing cap 47 (seen in FIG. 5) which screws onto the exterior threads of an adapter 49. An annular rubber gasket (not shown) is fitted to the interior of the cap 47 to press against the rim of the mouth formed by adapter 49 to prevent leaking. The adapter 49 is permanently secured to the mouth of the branch section 44 using PVC cement.

The sanitary tee joint 40, the bushings 45 and 46, and the cap 47 together form a cavity which surrounds an interior flow pipe 50 (seen in FIG. 2 through the cut-away section of the tee joint 40). Fluid passageways, one of which is seen at 51 and 52 in FIG. 2, are drilled at an angle through the interior flow pipe 50 to permit a portion of the flush water flow in pipe 50 to enter the surrounding additive reservoir cavity. The hole 52 is positioned downstream from the inlet hole 51 to return the diverted portion of the flow to the interior of flow pipe 50.

An additive (not shown), typically a disk of a commercially available water-soluble disinfectant/detergent/deodorant of the type normally placed in the tank of household toilets, is inserted into the mouth of the branch section 44 by removing the cap 47, and then resealing the cap 47 after the additive is in place.

Ring-shaped plastic bushings seen at 53 and 54 in FIG. 2 surround the interior pipe 50, maintaining a slidable friction fit with the pipe 50. The rings 53 and 54 may be moved axially along the length of the pipe 50 in order to restrict, to varying degrees, the flow through the passageways 51 and 52 respectively. By restricting the passageways 51 and/or 52, less fluid circulates past the additive disk, prolonging its life but reducing the amount of additive added to the fluid stream flowing though the interior pipe 50. If a solid disk additive is used, the rings 53 and 54 should be adjusted to cover 50% of each passageway. Alternatively, additive granules may be poured into the cavity, in which case the rings 53 and 54 should each be adjusted to cover 90% of the passageway openings. A screwdriver may be inserted through the mouth formed by the adapter 49 when the cap 47 is removed.

The tee joint 40 preferably takes the form of a standard sanitary pipe tee joint which presents three, 2-inch inside diameter mouth openings . . . Formed from plastic, the tee joint and the parts with which it mates are naturally resistant to the corrosive effects of seawater. The cylindrical shape of the transverse pipe section 42, in combination with the outwardly extending branch section 44, combine to form an additive reservoir cavity which promotes the desired flow of a diverted portion of the flush-water as well as adequate interior space to receive and retain the additive, while conforming to the flush water inlet conduit 13 to meet the confined spatial requirements of a marine toilet system. The ends of the transverse pipe section 42 of the tee joint 40 are suitably closed by the mating Genova 2×¾ plastic reducing bushings 45 and 46, both of which are also standard components sized to mate with the mouth openings presented by the tee joint 40. The bushings 45 and 46 are secured in place by conventional PVC cement. The interior flow pipe 50 is axially aligned with the transverse pipe section 42 of the tee joint 40 and is supported at each end by the bushings 45 and 46. The flow pipe 50 is formed from a 3-⅞" long section of ⅞" outside diameter Genova CPVC plastic tubing. The interior flow pipe 50, having a smaller outside diameter than the inside diameter of the bores 55 or 56, may be inserted through either bore and secured in place (about ¼ inch from the inner edge of each of the bushings 45 and 46) by means of hose washers seen at 65 and 66.

Figure 9:
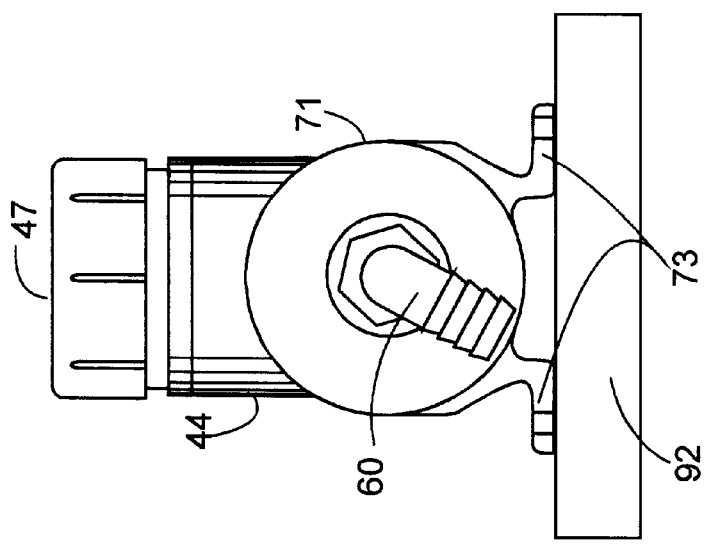
FIG. 7–9 are end elevational views of the injector unit shown mounted on structures having different orientations.
Figure 8:
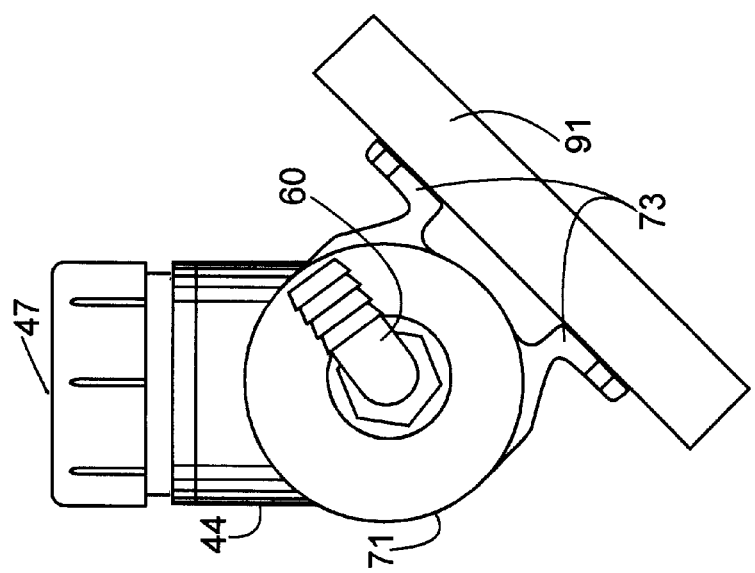
Figure 7:
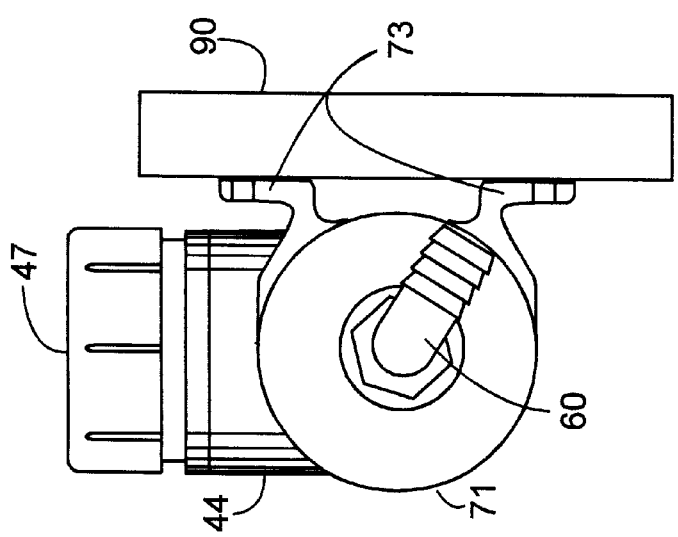

The bushings 45 and 46 have interior threaded bores 55 and 56 respectively which receive ¾ male-threaded right-angle barbed hose fittings (one of which is shown separately in FIG. 6) which are used to connect the injection unit 11 to the flush water inlet conduit. An annular resilient washer (not shown) may be inserted into each of the threaded bores 55 and 56 before the hose fittings are screwed into place, forming a water tight seal while permitting the hose fitting 60 to be rotated into a desired position with respect the body of the additive injection unit as depicted in FIGS. 7–9.

The plastic rings 53 and 54 may be easily removed and replaced in the unit 11 for periodic cleaning or adjustment by removing one of the hose washers 65 or 66 and pulling the flow pipe 50 half-way out of the tee joint, allowing the ring 54 to be reached for adjustment, removal or replacement through the mouth of branch section 44 (with cap 47 removed). The detachable cap 47 which mates with the adapter 49 and covers the mouth of the branch section 44 of the tee joint 40 is preferably fitted with an interior ring gasket (not shown) which provides a water-tight seal between the cap 47 and the adapter 49 which is cemented within the mouth of branch section 44.

It is desirable to position the additive injector so that the branch section 44 is directed upwardly so that the cap 47 may be removed to replace the additive disk without spilling the contents of the additive chamber. Moreover, it is desirable to secure the additive injector to a wall or other structure along the route of the water inlet tubing. To make it possible to secure the additive injector in a wide variety of environments which are typically cramped but otherwise widely varying in character, the present invention makes use of a novel rotatable mounting yoke shown separately in cross-section in FIG. 3. Each yoke, indicated generally at 70 in the drawings, is a single plastic molded part defining a cylindrical cup-shaped body section 71 and a pair of externally projecting mounting feet 73. An circular opening 75 centered on the circular face of the body section 71 provides an access passageway through which a hose connector 60 may be inserted and allowed to freely rotate. Each yoke 70 is independently rotatable with respect to the T-joint body 40, allowing the two yokes to be attached to uneven wall surfaces. The multiple orientations of the yokes and the hose fittings are illustrated in the FIGS. 7–9 of the drawings.

The interior diameter of the cup-shaped body section 71 of each mounting yoke is preferably 2-3/8", slightly larger than the outside diameter of the transverse body 42 of the T-joint, allowing the yoke to be readily inserted axially over the end of the T-joint and permitting it to rotate with respect to the T-joint. To insure a snug, vibration-free fit between the mounting jokes and the T-joint, O-rings seen at 81 and 82 in FIG. 2 are positioned in the annular groove formed between the T-joint and end adapters 45 and 46 respectively. The cup sections 71 of each yoke is pressed over the O-ring and mounting screw passing through a slot 88 in foot 73 of the yoke secures the yoke an adjoining mounting surface.

It is to be understood that the embodiment of the invention which has been described is merely illustrative of one application of the principles of the invention. Numerous modifications may be made by those skilled in the art without departing from the true spirit and scope of the invention.

What is claimed is:

1. An additive injection unit for a toilet system comprising, in combination, an elongated housing comprising a substantially T-shaped hollow chamber defining a transverse cylindrical passageway and a perpendicular branch passageway, said housing adapted for connection in series with an input pipe for carrying a water stream directed to a toilet and for injecting an additive into said water stream, said branch passageway having a mouth forming an access opening through which additive can be inserted into said housing, and first and second mounting members having hollow cylindrical sections shaped to fit over and conform to a respective end of said transverse passageway, each of said mounting members being individually rotatable with respect to said housing and defining a mounting surface adapted to bear against and be supported by a base structure, and a resilient O-ring positioned between each of the mounting members and the respective end of said transverse passageway for providing a friction fit between said mounting members and said housing which permits said mounting members to rotate and move axially with respect to transverse passageway while securing said housing in place with respect to said mounting members.

2. An additive injection unit as set forth in claim 1 including a cap for covering said access passageway to retain fluids within said housing while permitting access to the interior of said housing when removed.

3. An additive injection unit as set forth in claim 2 wherein said housing may be rotated with respect to said mounting members and said base structure to position said access opening above said transverse passageway to reduce spillage when said cap is removed.

4. An arrangement for introducing an additive into a fluid flow which comprises, in combination, a flow pipe formed from corrosion resistant plastic having a uniform diameter, means for connecting said flow pipe in series fluid-flow with a conduit, said means for connecting said flow pipe being formed from corrosion resistant plastic, a closed additive reservoir cavity formed by a main body section of said arrangement surrounding said flow pipe, said means for connecting said flow pipe in series flow relation, and a twist-on sealing cap covering an access passageway, said additive reservoir cavity comprising, in combination, a sanitary pipe tee joint having first and second circular mouths at opposing ends of a cylindrical transverse body pipe section and a third circular mouth at the outer end of a branch pipe section which extends radially outward from the middle of said transverse body pipe section, first and second annular size-reduction bushings inserted in and affixed to the said first and second mouths respectively for removably securing opposing ends of said flow pipe in a position extending axially through said transverse body pipe section, at least one inlet aperture and at least one return aperture through said flow pipe, both of said apertures providing a fluid flow path between the interior of said pipe and said additive reservoir cavity, and said inlet aperture being positioned upstream from said return aperture to induce a portion of the fluid flowing through said conduit to flow through said additive reservoir cavity, said access passageway leading into said additive reservoir cavity and being normally covered by said removable twist-on sealing cap which may be opened to permit an additive material to be introduced into said additive reservoir cavity and thereafter closed to provide a pressure tight seal for said additive reservoir cavity and to retain said material within said additive reservoir cavity, and a pair of mounting yokes mounted for rotational movement to each end of said transverse body pipe section, each of said mounting yokes defining mounting feet having a bearing surface for individual engagement with and attachment to an available base structure, and a resilient O-ring positioned between each of the mounting yokes and said transverse body pipe section for providing a friction fit between said mounting yokes and said body pipe section which permits said mounting yokes to rotate and move axially with respect to said body pipe section while securing said body pipe section in place with respect to said mounting yokes.

5. An arrangement as set forth in claim 4 further comprising adjustable means for variably restricting the fluid flow path through said inlet aperture, said additive reservoir cavity, and said return aperture whereby the volume of fluid diverted through said additive reservoir cavity may be adjusted to vary the amount of additive introduced into said conduit.

* * * * *